(12) United States Patent
Shakya et al.

(10) Patent No.: US 7,655,801 B2
(45) Date of Patent: Feb. 2, 2010

(54) SUBSTITUTED CARBAMIC ACID QUINOLIN-6-YL ESTERS USEFUL AS ACETYLCHOLINESTERASE INHIBITORS

(75) Inventors: Neeraj Shakya, Uttar Pradesh (IN); Zeeshan Fatima, Uttar Pradesh (IN); Chandishwar Nath, Uttar Pradesh (IN); Anil Kumar Saxena, Uttar Pradesh (IN)

(73) Assignee: Council of Scientific and Industrial Research, New Dehli (IN)

( * ) Notice: Subject to any disclaimer, the term of this patent is extended or adjusted under 35 U.S.C. 154(b) by 410 days.

(21) Appl. No.: 11/022,924

(22) Filed: Dec. 28, 2004

(65) Prior Publication Data
US 2006/0142335 A1    Jun. 29, 2006

(51) Int. Cl.
*C07D 215/38* (2006.01)
*A61K 31/48* (2006.01)

(52) U.S. Cl. .................. 546/176; 546/177; 514/312
(58) Field of Classification Search .................. 546/176, 546/177; 514/312
See application file for complete search history.

(56) References Cited

U.S. PATENT DOCUMENTS

| 3,997,542 A | 12/1976 | Bailey |
| 4,472,404 A | 9/1984 | Paxton et al. |

FOREIGN PATENT DOCUMENTS

| EP | 0 175 005 | * | 3/1986 |
| EP | 1382598 A1 | | 1/2004 |

| ZA | 8407058 | * | 4/1985 |

OTHER PUBLICATIONS

Musser, J Med Chem, vol. 30, pp. 62-67, 1987.*
Bailey, J Med Chem, vol. 22, No. 5, pp. 599-601, 1979.*
International Search Report—Aug. 5, 2005.

* cited by examiner

*Primary Examiner*—D. Margaret Seaman
(74) *Attorney, Agent, or Firm*—Nixon & Vanderhye

(57) ABSTRACT

The present invention relates to new substituted carbamic acid quinoline-6-yl esters of formulae 1 and 2 where $R_1$=alkyl, aryl; $R_2$=H, alkyl, aralkyl useful as acetylcholinesterase inhibitors, and which show potent antiacetylcholinesterase activity and have potential therapeutic use for prevention or cure of acetylcholinesterase related disorders including peripheral as well as central nervous system.

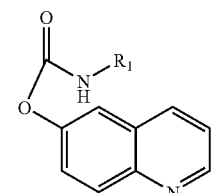

1

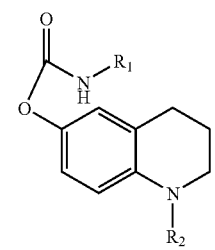

2

17 Claims, 1 Drawing Sheet

SUBSTITUTED CARBAMIC ACID QUINOLIN-6-YL ESTERS USEFUL AS ACETYLCHOLINESTERASE INHIBITORS

FIELD OF THE INVENTION

The present invention relates to novel derivatives of quinolinyl carbamic acid esters. The present invention particularly relates to new substituted carbanic acid quinolinyl esters useful as acetylcholinesterase inhibitors, which show potent anti-acetylcholinesterase activity and have potential therapeutic use for prevention or cure of Alzheimer's disease, senile dementia or memory disturbance. The present invention particularly relates to compounds of the formulae 1 and 2

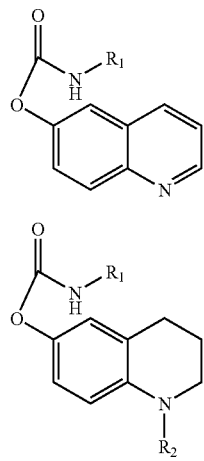

wherein $R_1$=alkyl, aryl; $R_2$=H, alkyl, aralkyl.

BACKGROUND OF THE INVENTION

Alzheimer's disease (AD) is a chronic neurodegenerative disorder. The characteristic symptom of AD in the patient is gradual decline in cognitive function. Despite several approaches to the treatment of this disorder, still there is no well-approved therapy to check the progression of AD except the inhibition of acetylcholinesterase (AChE). The currently available drugs used for AD include donepezil (Bryson, H. M.; Benfield, P. *Drugs Aging* 1997, 10, 234), galanthamine (Fulton, B.; Benfield, P, *Drugs Aging,* 1996, 9, 60), tacrine (Summers, W. K., Majovski, L. V.; Marsh, G. M.; Tachiki, K.; Kling, A., *The New England Journal of Medicine,* 1946, 315, 1241; Wagstaff, A. J.; McTavish, D. *Drugs Aging* 1994, 4, 510), rivastigmine (Spencer, C. M., Noble, S. *Drugs Aging* 1998, 13, 391) and memantine (Möbius, H. J.; Stöffler, A.; Graham, S. M. *Drugs of Today,* 2004, 40, 685). The major side effects associated with most of these drugs are liver toxicity, headache, fatigue, dizziness, nausea, vomiting, loss of appetite, joint pain, insomnia etc. Apart from these drugs several other molecules have shown potent activity in different test models including animal models. Some of these are xanthostigmine (Rampa, A., Piazzi, L; Bulleti, F.; Gobbi, S.; Bisi, A.; Bartolini, M.; Andrisano, V.; Cavrini, V., Cavalli, A.; Recanatini, M., Valenti, P. *J. Med. Chem.,* 2001, 44, 3810), physostigmine (Moeller H. J., Hampel H.; Hegerl U.; Schmitt W. and Walter K. *Pharmacopsychiatry* 1999, 32, 99), phenserine (Al-Jafari A. A., Kamal, M. A., Greig, N. H. *J. Physiol.,* 1998, 92, 402), Huperzine-A (Kozikowsky, A. P., Campiani, G., Sun, L. Q., Wang, S.; Saxena, A.; Doctor, B. P. *J. Am. Chem. Soc.,* 1996, 118, 11357), bis-tacrine (Pang, Y. P. Quiram, P; Jelacio, T; Hong, F., Brimjoin, S. *J. Biol. Chem.,* 1996, 271, 23646) etc. As the average age is increasing all over the world, and so the AD (18 million people worldwide; 66% people in developing countries), there is an urgent need to identify novel candidate molecule for drug development.

OBJECTS OF THE INVENTION

The main object of the present invention is to provide novel molecules incorporating quinoline flanked on one side by carbamic acid ester and on the other side hydrogen or alkyl like methyl or aralkyl like benzyl groups that exhibit better therapeutic efficacy to treat dementia of Alzheimer's type.

It is another object of the invention to provide a method for the treatment of Alzheimer's disease.

It is a further object of the invention to provide compounds useful for the treatment or prevention of senile dementia of Alzheimer's type, vascular dementia, alcoholic dementia, dementia associated with neurological disorders such as epilepsy, neoplasm and post-trauma and dementia related with behavioral disorders like depression.

It is another object of the invention to provide compounds useful for the treatment or prevention of atony of the smooth muscle of the intestinal tract (paralytic ileus) and atony of urinary bladder.

It is another object of the invention to provide compounds useful for the treatment or prevention of glaucoma and myasthenia gravis.

SUMMARY OF THE INVENTION

Accordingly the present invention provides a quinoline derivative represented by formula 1 and 2 below:

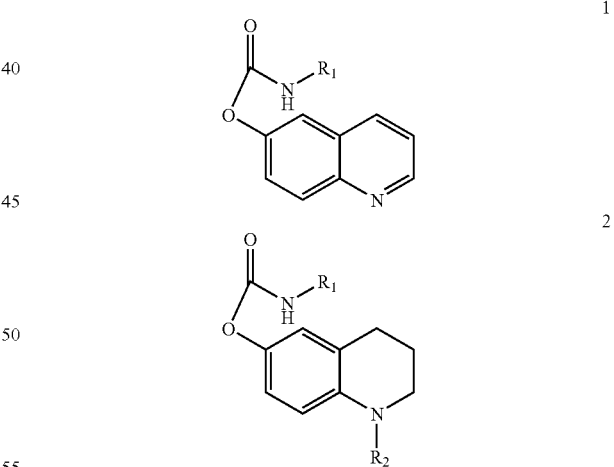

wherein $R_1$=alkyl, aryl; $R_2$=H, alkyl, aralkyl.

In one embodiment of the invention, the substituted carbamic acid quinolinyl esters obtained are selected from the group consisting of:
1a. hexyl-carbamic acid quinolin-6-yl ester
1b. heptyl-carbamic acid quinolia-6-yl ester
1c. (2-choro-phenyl)-carbamic acid quinolin-6-yl ester
1d. (3-bromo-phenyl)-carbamic acid quinolin-6-yl ester
2a. hexyl-carbamic acid 1, 2, 3, 4-tetrahydro-quinolin-6-yl ester 2b. heptyl-carbamic acid 1, 2, 3, 4-tetrahydro-quinolin-6-yl ester
2c. (3-bromo-phenyl)-carbamic acid 1,2,3,4-tetrahydro-quinolin-6-yl ester
2d. (2-chloro-phenyl)-carbamic acid 1, 2, 3, 4-tetrahydro-quinolin-6-yl ester
2e. (4-chloro-3-trifluoromethyl-phenyl)-carbamic acid 1, 2, 3, 4-tetrahydro-quinolin-6-yl ester
2f. (4-bromo-phenyl)-carbamic acid 1, 2, 3, 4-tetrahydro-quinolin-6-yl ester
2g. heptyl-carbamic acid 1-benzyl-1, 2, 3, 4-tetrahydro-quinolin-6-yl ester
2h. hexyl-carbamic acid 1-benzyl-1, 2, 3, 4-tetrahydro-quinolin-6-yl ester
2i. (2-chloro-phenyl)-carbamic acid 1-benzyl-1, 2, 3, 4-tetrahydro-quinolin-6-yl ester
2j. (3-bromo-phenyl)-carbamic acid 1-benzyl-1, 2, 3, 4-tetrahydro-quinolin-6-yl ester
2k. (4-chloro-3-trifluoromethyl-phenyl)-carbamic acid 1-benzyl-1, 2, 3, 4-tetrahydro-quinolin-6-yl ester
2l. (4-bromo-phenyl)-carbamic acid 1-benzyl-1, 2, 3, 4-tetrahydro-quinolin-6-yl ester
2m. hexyl-cabamic acid 1-methyl-1, 2, 3, 4-tetrahydro-quinolin-6-yl ester
2n. heptyl-carbamic acid 1-methyl-1, 2, 3, 4-tetrahydro-quinolin-6-yl ester
2o. (2-chloro-phenyl)-carbamic acid 1-methyl-1, 2, 3, 4-tetrahydro-quinolin-6-yl ester
2p. (3-bromo-phenyl)-carbamic acid 1-methyl-1, 2, 3, 4-tetrahydro-quinolin-6-yl ester
2q. (4-chloro-3-trifluoromethyl-phenyl)-carbamic acid 1-methyl-1, 2, 3, 4-tetrahydro-quinolin-6-yl ester
2r. (4-bromo-phenyl)-carbamic acid 1-methyl-1, 2, 3, 4-tetrahydro- quinolin-6-yl ester The present invention also provides a process for the synthesis of a quinoline derivative represented by formula 1 and 2 below:

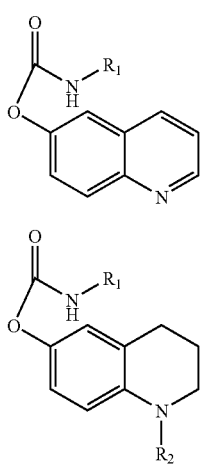

wherein $R_1$=alkyl, aryl; $R_2$=H, alkyl, aralkyl, the process comprising reacting a substituted phenol with an isocyanate in the presence of abase and at least one organic solvent using a base and at least one organic solvent to obtain the corresponding carbamic acid ester (carbamate) of formulae 1 or 2.

In one embodiment of the invention, $R_1$ is selected from the group consisting of hexyl and heptyl.

In another embodiment of the invention, when $R_1$ is aryl it is selected from the group consisting of 2- chloro, 3-bromo, 4-bromo and 4-chloro-3-trifluoromethyl-phenyl.

In another embodiment of the invention, $R_2$ is selected from the group consisting of methyl and beazyl.

In another embodiment of the invention, the base used is selected from an organic or an inorganic base.

In another embodiment of the invention, the solvent is selected from the group consisting of ether, tetrahydrofuran (THF), dimethylformamide (DMF), dioxane, dichloromethane and chloroform.

In another embodiment of the invention, the base is selected from the group consisting of sodium hydride, sodium hydroxide, triethylamine and pyridine.

In yet another embodiment of the invention, the reaction is carried out at a temperature in the range of −10° C. to 80° C. and for a period between half an hour to 100 hours.

In another embodiment of the invention, the reaction is carried out in the presence of a catalyst selected from the group consisting of sodium iodide and potassium iodide.

In another embodiment of the invention the molar ratio of substituted phenol to isocyanate is in the range of 1:1 to 1:1.2.

In another preferred embodiment of the invention, the organic solvent is present in an amount in the range of 1.0 ml to 10 ml per mmol of the reactants.

In another embodiment of the invention, the compounds of formulae 2g. heptyl-carbamic acid 1-benzyl-1, 2, 3, 4-tetrahydro-quinolin-6-yl ester
2h. hexyl-carbaric acid 1-benzyl-1, 2, 3, 4-tetrahydro-quinolin-6-yl ester
2i. (2-chloro-phenyl)-carbamic acid 1-benzyl-1, 2, 3, 4-tetrahydro-quinolin-6-yl ester
2j. (3-bromo-phenyl)-carbamic acid 1-benzyl-1, 2, 3, 4-tetrahydro-quinolin-6-yl ester
2k. (4-chloro-3-trifluoromethyl-phenyl)-carbamic acid 1-benzyl-1, 2, 3, 4-tetrahydro-quinolin-6-yl ester
2l. (4-bromo-phenyl)-carbamic acid 1-benzyl-1, 2, 3, 4-tetrahydro-quinolin-6-yl ester
2m. hexyl-carbamic acid 1-methyl-1, 2, 3, 4-tetrahydro-quinolin-6-yl ester
2n. heptyl-carbamic acid 1-methyl-1, 2, 3, 4-tetrahydro-quinolin-6-yl ester
2o. (2-chloro-phenyl)-carbamic acid 1-methyl-1, 2, 3, 4-tetrahydro-quinolin-6-yl ester
2p. (3-bromo-phenyl)-carbamic acid 1-methyl-1, 2, 3, 4-tetrahydro-quinobin-6-yl ester
2q. (4-chloro-3-trifluoromethyl-phenyl)-carbamic acid 1-methyl-1, 2, 3, 4-tetrahydro-quinolin-6-yl ester
2r. (4-bromo-phenyl)-carbamic acid 1-methyl-1, 2, 3, 4-tetrahydro-quinolin-6-yl ester are obtained from 2a-f
2a. hexyl-carbamic acid 1, 2, 3, 4-tetrahydro-quinolin-6-yl ester
2b. heptyl-carbamic acid 1, 2, 3, 4-tetrahydro-quinolin-6-yl ester
2c. (3-bromo-phenyl)-carbamic acid 1,2,3,4-tetrahydro-quinolin-6-yl ester
2d. (2-chloro-phenyl)-carbamic acid 1, 2, 3, 4-tetrahydro-quinolin-6-yl ester
2e. (4-chloro-3-trifluoromethyl-phenyl)-carbamic acid 1, 2, 3, 4-tetrahydro-quinolin-6-yl ester
2f. (4-bromo-phenyl)-carbamic acid 1, 2, 3, 4-tetrahydro-quinolin-6-yl ester by first reacting compounds 2a-l with an alkyl or aralkyl halide of formula RX wherein R is at least methyl or benzyl group and X is selected from chloro, bromo and iodio using a solvent selected from the group consisting of dimethylformamide, tetrahydrofuran and dioxane, in the presence of an organic or inorganic base selected from the group consisting of sodium hydride, sodium hydroxide, triethylamine and pyridine and at a temperature ranging between −10° C. to 37° C. for a period of 1 hour to 12 hours in the presence or absence of a catalyst sodium iodide or potassium iodide.

In another embodiment of the invention, compounds of formulae 2a-f are synthesized from 2m-r using Pd—C 5-10% catalyst in a solvent selected from group consisting of ethanol and methanol in an amount of 15-25 ml per mmol of compound, by applying hydrogen pressure in the range of 50-60 psi for a period between 4-12 hours at room temperature.

In another embodiment of the invention, the phenol is reacted with an isocyanate to obtain corresponding carbamate which is then reduced with Ni—Al alloy/KOH/ethanol to give corresponding 1, 2, 3, 4-tetrahydro derivatives of formula 2a-l.

In another embodiment of the invention, the phenol is reacted with an isocyanate to obtain corresponding N-benzyl derivatives 2m-r which are then debenzylated using 5% or 10% Pd—C/$H_2$ in ethanol or methanol as solvent to obtain the corresponding debenzylated carbamates of formulae 2a-f, which are then N-methylated using MeI to give compounds of formulae 2m-r.

In another embodiment of the invention, compounds of formulae 2a-l are methylated in the presence of a solvent selected from the group consisting of tetrahydrofuran, dioxane and dimethylformamide and at a temperature ranging from 10 to 37° C., for between 3 hours to 48 hours.

The present invention also comprises a method for the treatment of hypofunctioning of cholinergic system in a subject, comprising administering a pharmaceutically effective amount of compound of formulae 1 or 2

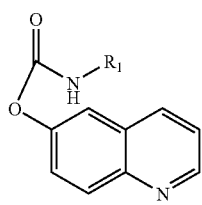

1

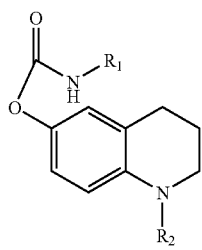

2 wherein $R_1$=alkyl, aryl, $R_2$=H, alkyl, aralkyl, to a subject suffering from hypofunctioning of cholinergic system.

In one embodiment of the invention, the hypofunctioning of cholinergic system occurs in the peripheral or central nervous system of the subject.

In another embodiment of the invention, the hypofunctioning of cholinergic system results in atony of smooth muscle of intestinal tract, atony of urinary bladder, glaucoma, myasthenia gravis and cognitive behaviour dysfunction of the subject.

In another embodiment of the invention, the subject is a mammal.

In yet another embodiment of the invention, the mammal is a human being.

DETAILED DESCRIPTION OF THE INVENTION

Figure 1:
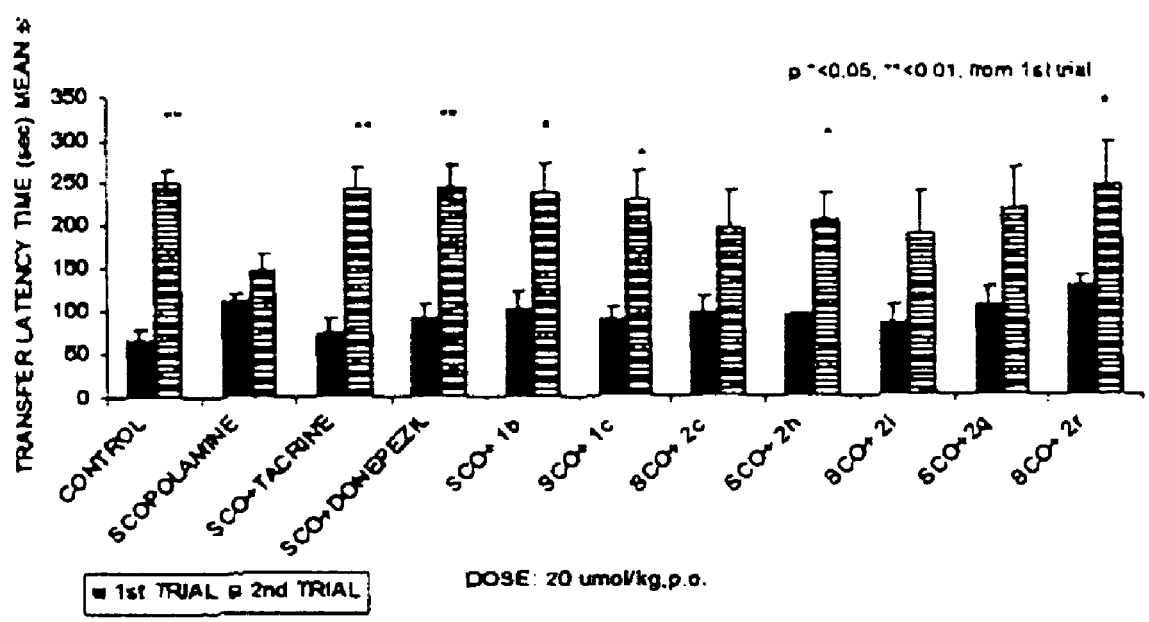
FIG. 1 represents scopolamine induced deficit (dementia/amnesia) in mice Passive Avoidance Test.

The main objects of the present invention are:
1. provide novel molecules incorporating quinoline flanked on one side by carbamic acid ester and on the other side hydrogen or alkyl like methyl or aralkyl like benzyl groups that exhibit better therapeutic efficacy to treat dementia of Alzheimer's type.
2. provide a method treating Alzheimer's disease. In formulae 1 and 2, the $R_1$ is alkyl group like hexyl, heptyl etc.; the aryl group is substituted phenyl like trifluromethyl and halophenyl wherein halo is chloro, bromo etc. The $R_2$ group is like methyl, benzyl etc.
3. provide useful compounds for the treatment or prevention of senile dementia of Alzheimer's type.
4. provide useful compounds for the treatment or prevention of vascular dementia.
5. provide useful compounds for the treatment or prevention of alcoholic dementia.
6. provide useful compounds for the treatment or prevention of dementia associated with neurological disorders such as epilepsy, neoplasm and post-trauma.
7. provide useful compounds for the treatment or prevention of dementia related with behavioral disorders like depression.
8. provide useful compounds for the treatment or prevention of atony of the smooth muscle of the intestinal tract (paralytic ileus).
9. provide useful compounds for the treatment or prevention of atony of urinary bladder.
10. provide useful compounds for the treatment or prevention of glaucoma.
11. provide useful compounds for the treatment or prevention of myasthenia gravis.

The above objects of the invention are achieved by novel pharmacologically active substances specifically substituted carbamic acid quinolinyl esters of the formula 1 and 2,

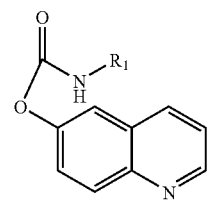

1

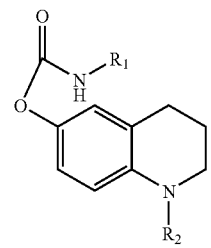

2 where $R_1$=alkyl, aryl; $R_2$=H, alkyl, aralkyl, Representative compounds include:
1a. hexyl-carbamic acid quinolin-6-yl ester
1b. heptyl-carbamic acid quinolin-6-yl ester
1c. (2-chloro-phenyl)-carbamic acid quinolin-6-yl ester
1d. (3-bromo-phenyl)-carbamic acid quinolin-6-yl ester
2a. hexyl-carbamic acid 1, 2, 3, 4-tetrahydro-quinolin-6-yl ester
2b. heptyl-carbamic acid 1, 2, 3, 4-tetrahydro-quinolin-6-yl ester
2c. (3-bromo-phenyl)-carbamic acid 1,2,3,4-tetrahydro-quinoline-6-yl ester
2d. (2-chloro-phenyl)-carbamic acid 1, 2, 3, 4-tetrahydro-quinolin-6-yl ester
2e. (4-chloro-3-trifluoromethyl-phenyl)-carbamic acid 1, 2, 3, 4-tetrahydro-quinolin-6-yl ester
2f. (4-bromo-phenyl)-carbamic acid 1, 2, 3, 4-tetrahydro-quinolin-6-yl ester
2g. heptyl-carbamic acid 1-benzyl-1, 2, 3, 4-tetrahydro-quinolin-6-yl ester
2h. hexyl-carbamic acid 1-benzyl-1, 2, 3, 4-tetrahydro-quinolin-6-yl ester
2i. (2-chloro-phenyl)-carbamic acid 1-benzyl-1, 2, 3, 4-tetrahydro-quinolin-6-yl ester
2j. (3-bromo-phenyl)-carbamic acid 1-benzyl-1, 2, 3, 4-tetrahydro-quinolin-6-yl ester
2k. (4-chloro-3-trifluoromethyl-phenyl)-carbamic acid 1-benzyl-1, 2, 3, 4-tetrahydro-quinolin-6-yl ester
2l. (4-bromo-phenyl)-carbamic acid 1-benzyl-1, 2, 3, 4-tetrahydro-quinolin-6-yl ester
2m. hexyl-carbamic acid 1-methyl-1, 2, 3, 4-tetrahydro-quinolin-6-yl ester
2n. heptyl-carbamic acid 1-methyl-1, 2, 3, 4-tetrahydro-quinolin-6-yl ester
2o. (2-chloro-phenyl)-carbamic acid 1-methyl-1, 2, 3, 4-tetrahydro-quinolin-6-yl ester
2p. (3-bromo-phenyl)-carbamic acid 1-methyl-1, 2, 3, 4-tetrahydro-quinolin-6-yl ester
2q. (4-chloro-3-trifluoromethyl-phenyl)-carbamic acid 1-methyl-1, 2 ,3, 4-tetrahydro-quinolin-6-yl ester
2r. (4-bromo-phenyl)-carbamic acid 1-methyl-1, 2, 3, 4-tetrahydro-quinolin-6-yl ester The compounds of the invention are prepared by reacting substituted phenols with various isocyanates. In such cases $R_1$ includes at least alkyl like hexyl, heptyl and aryl like 2-chloro, 3-bromo, 4-bromo, 4-chloro-3-trifluoromethyl-phenyl, $R_2$ includes at least methyl or benzyl group. The reaction is carried out using organic and inorganic bases and at least one organic solvent such as ether, tetrahydrofuran (THF), dimethylformamide (DMF), dioxane, dichloromethane or chloroform and at temperature ranging from $-10°$ C. to $80°$ C. for a period between half an hour to 100 hours to produce corresponding carbamic acid esters (carbamates).

The synthesis of compounds of formula 2g-r from 2a-f is achieved by reacting compounds 2a-l with RX (alkyl or aralkyl halides) wherein R includes at least methyl or benzyl group and X includes at least chloro, bromo or iodio and using a solvent such as DMF, THY and dioxane, in the presence of an organic or inorganic base such as sodium hydride, sodium hydroxide, triethylamine or pyridine at a temperature ranging between $-10°$ C. to $37°$ C. for a period of 1 hour to 12 hours in the presence or absence of a catalyst sodium iodide or potassium iodide.

The molar ratio of substituted phenols to isocyanate is 1:1 to 1:1.2. In yet another preferred embodiment of the present invention, the organic solvent is present about 1.0 ml to 10 ml per mmol of the compounds. Preferably, 2a-f are synthesized from 2m-r using Pd—C 5-10% in the solvents like ethanol or methanol (15-25 ml for per mmol of the compound) by applying hydrogen pressure 50-60 psi for a period between 4-12 hours at room temperature. Salts of the compounds types 1 and 2 are also included within the scope of the invention.

The invention also relates to a method for enhancing cholinergic activity in conditions linked with hypofunctioning of cholinergic system. Such situations include peripheral as well as central nervous system. Peripheral nervous system disorders in which use of anticholinesterse is indicated are atony of the smooth muscle of the intestinal tract (paralytic ileus), stony of urinary bladder, glaucoma, and myasthenia gravis. In central nervous system the most important area is cognitive behaviour dysfunctions (dementia).

The compound of formula 1 and 2m-r of the present invention are prepared by one of the following process shown in the following scheme.

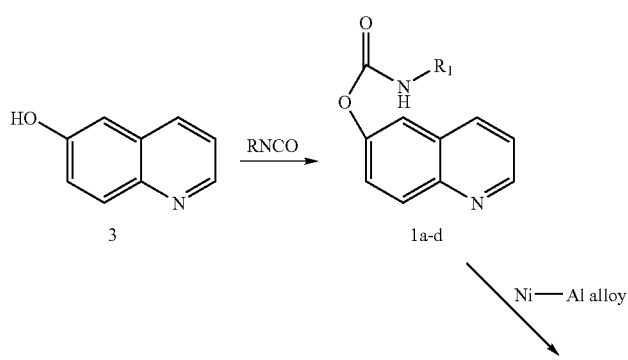

-continued

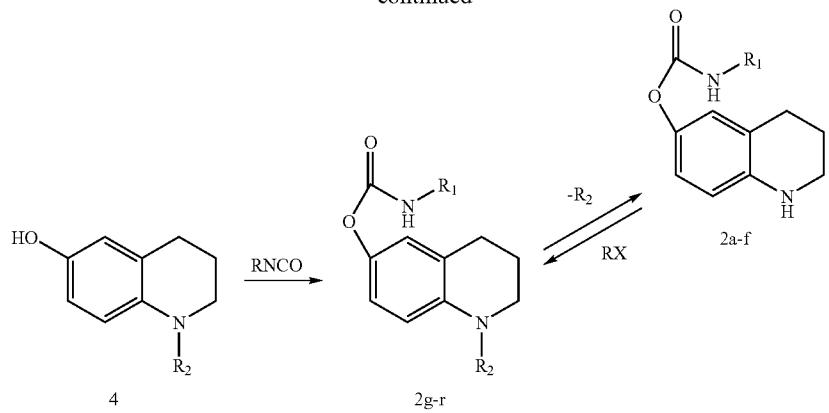

wherein $R_1$=alkyl, aryl; $R_2$=alkyl, aralkyl

The phenols 3 and 4 in the above scheme were reacted with various isgocyanates to give corresponding carbamates. The carbamates 1a-d were further reduced with Ni—Al alloy/KOH/ethanol to give the corresponding 1, 2, 3, 4-tetrahydro derivatives 2a-l. The N-benzyl derivatives 2m-r were debenzylated using 5% or 10% Pd—C/$H_2$ in ethanol or methanol as a solvent to give corresponding debenzylated carbamates 2a-f. These debenzylated carbamates were then N-methylated using MeI to give 2m-r.

The phenols 3 and 4 in the above scheme, were converted to the corresponding isocyanates using solvents such as tetrahydrofuran, dioxane, dimethylformamide, dichloromethane or chloroform, in the presence of bases like sodium hydride, sodium hydroxide, potassium hydroxide, sodium carbonate, potassium carbonate, pyridine or triethylamine at a temperature ranging from –10° C. to 80° C. for ½ hour to 100 hours. In methylation of compounds 2a-l various solvents were used like tetrahydrofuran, dioxane and dimethylformamide at a temperature ranging from 10 to 37° C., for between 3 hours to 48 hours.

The present invention deals with the synthesis and evaluation of various novel substituted carbamic acid quinolinyl esters represented by formulae 1 and 2 for their antiacetylcholinesterase inhibitory activity. These compounds have shown very high antiacetylcholinesterase inhibitory activity when compared with prior art compounds illustrated below.

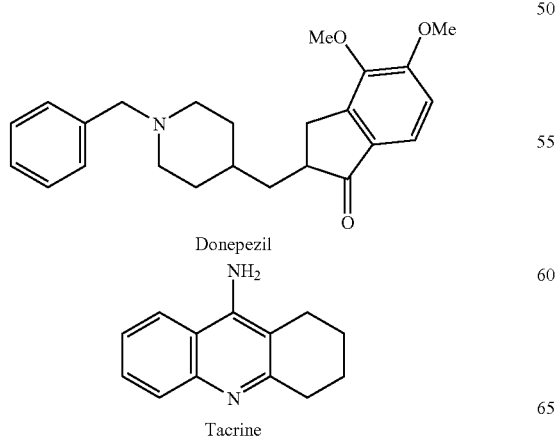

Donepezil

Tacrine

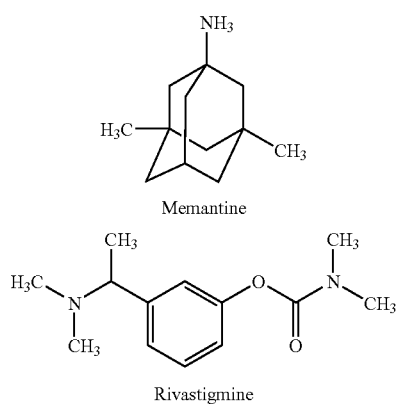

Memantine

Rivastigmine

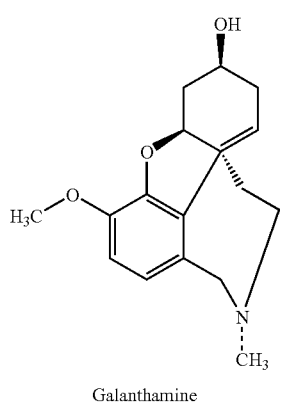

Galanthamine

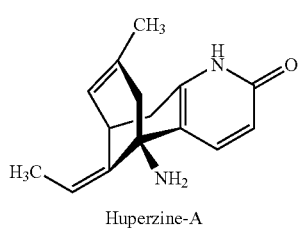

Huperzine-A

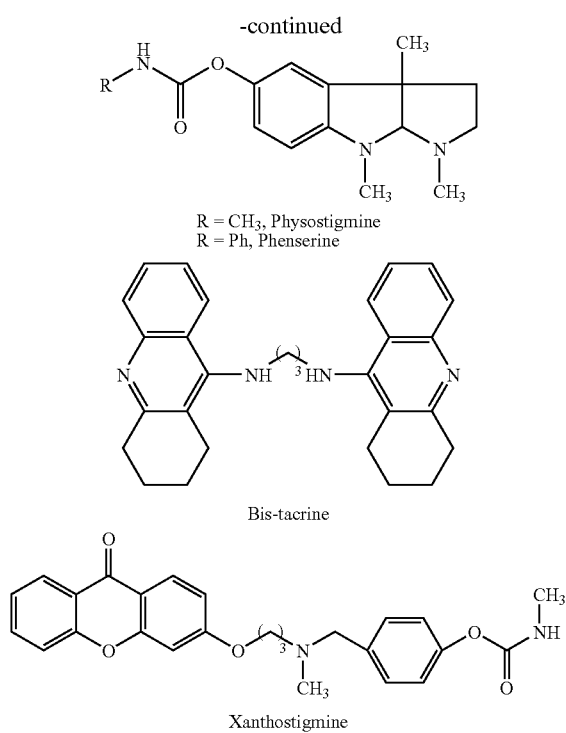

R = CH$_3$, Physostigmine
R = Ph, Phenserine

Bis-tacrine

Xanthostigmine

Pharmacological Action of Compounds 1 and 2

Pharmacological action of the compounds of the present invention was tested using several compounds prepared in examples presented herein after and tacrine and donepezil as a comparative compound.

(A) Inhibitive Effect on Acetylcholinesterase Activity

The study was conducted in adult SD male rats (200-250 g) Rats were perfused under mild ether anesthesia through heart with ice cooled normal saline (0.9% NaCl) to reduce blood-borne cholinesterase from brain. After perfusion whole brain was taken out. 10% (w/v) homogenate of brain was prepared first by homogenizing in Ultra-Turrax T25 homogenizer at a speed of 9500 rpm thrice giving intervals for few seconds in between the runs, with sodium phosphate buffer (30 mmol/lit, pH 7.0). Sodium phosphate buffer was taken in a volume half to the final volume required for 10% homogenate. 1% Triton X-100 (1% w/v in 30 mmol/lit. sodium phosphate buffer, pH 7.0) is then added in a volume to make the final volume for 10% homogenate, slowly while stirring the homogenate on ice.

The homogenate was centrifuged at 100,000×g at 4° C. in a Beckman Ultracentrifuge (LE 80) using a fixed angle rotor (80 Ti) for 60 min. Supernatant was collected and stored at 4° C. Aliquots of this supernatant was diluted in the ratio of 1:10 and used as a source of enzyme for the assay.

Enzyme Assay:

Assay of AChE was performed according to method described by Ellman et al., (Ellman, G. E.; Courtney, K. D.; Andersen, V. Jr.; Featherstone, R. M. *Biochem. Pharmacol.* 1961, 7, 88). Kinetic profile of the enzyme activity was studied spectrophotometrically at 412 nm at an interval of 15 s. Assay for each sample was run in duplicate and each experiment was performed thrice. The specific activity of AChE was calculated by following formula:

AChE activity=$\Delta E \times 1000 \times V / 1.36 \times 10000 \times v$ $\Delta E$=Extinction change/min
1000=Conversion factor for μmoles
V=Volume of the total reaction mixture
1.36×10000=Extinction Coefficient
v=volume of the enzyme used The specific activity of AChe is expressed in μmoles/min/mg of protein.

The test substance (dissolved in DMSO) was incubated with enzyme source in concentration of 100 μg/1 ml of reaction mixture for 30 min at 37° C. prior to obtain kinetic profile of AChE activity. Tacrine (1 μmol) was used as standard AChE inhibitor (standard control). The AChe inhibitory activity was calculated on the basis of % decrease change from control values i.e. AChe acivity without incubation with any standard or test drug.

Protein Assay:

Protein was estimated in the brain samples by modified Lowry's method (Wang, C. H.; Smith, R. L *Anal. Biochem.* 1975, 63, 414). Bovine serum albumin (BSA) was used as standard in the concentration of 1 mg/ml. was estimated in the range of 0.01-0.1 mg/ml.

TABLE 1

Cholinesterase Enzyme Activity (μmol/mg of protein/min) in presence of different concentrations of active drug

| Drug | (Conc. μm) | | | | |
| --- | --- | --- | --- | --- | --- |
|  | 0.1 | 0.3 | 1 | 3 | 10 |
| Tacrine | 0.01258 | 0.01165 | 0.0027 | 0.0018 | 0.0004 |
| 2i | 0.01351 | 0.01211 | 0.01071 | 0.007456 | 0.001864 |

TABLE 2

% Cholinesterase Enzyme Activity in presence of different concentrations of active drug

| Drug | (Conc. μm) | | | | |
| --- | --- | --- | --- | --- | --- |
|  | 0.1 | 0.3 | 1 | 3 | 10 |
| Tacrine | 87.09 | 80.64 | 19.35 | 12.90 | 3.22 |
| 2I | 93.54 | 83.87 | 74.19 | 51.61 | 12.90 |

Control AChE activity = 0.014446 (μmol/mg of protein/min)

TABLE 3

% Anticholinesterase Enzyme Inhibition in presence of different concentrations of active drug

| Drug | (Conc. μm) | | | | | IC$_{50}$ μm |
| --- | --- | --- | --- | --- | --- | --- |
|  | 0.1 | 0.3 | 1 | 3 | 10 |  |
| Tacrine | 12.90 | 19.35 | 80.64 | 87.09 | 96.77 | 0.8 |
| 2i | 6.45 | 16.12 | 25.80 | 48.38 | 87.09 | 3.31 |

(B) Effects on Amnesia Induced by Scopolamine in mice

Experimental procedures

Single trial passive avoidance is widely used as experimental test to assess learning memory functions in rodents. Scopolamine induced impairment in passive avoidance (in vivo) and inhibition of acetylcholinesterase (in vitro) in rodents are commonly employed and screening test to predict potential of an acetylcholinesterase inhibitor as cognitive enhancer (antidementic) drug (Das, A.; Shanker, G.; Nath C; Pal, R; Singh, S; Singh, H. K; *Pharmacol. Biochem. Behav.* 2002, 73, 893).

Passive Avoidance Test (in vivo): Study was conducted in adult Swiss male mice of 3-4 months (wt. 20-25 g) which were kept in standard housing condition with 12 h light and dark cycle. Food and water were available ad libitum. Mice were subjected to single trial passive avoidance test described by Brioni (Brioni, J. D.; Hock, F. J.; McGaugh, J. J. Drug effects on learning and memory in: Vogel, G. H. and Vogel, W. H. (Eds.), Drug Discovery and Evaluation: Pharmacological Assays. Springer Verlag Press, New York,. 1997, pp. 335-336). Passive avoidance test was studied by a computerized shuttle box (Columbus Instruments, Ohio, USA) provided with a software program PACS 30. The shuttle box comprises of two compartments, isolated by an automated door. After exploration period of 30 s for acclimatization the animal was subjected to a trial of 270 seconds. Each mouse was placed in the bright compartment and on transfer into the dark compartment it was given an electric shock (0.5 mA for 5 s) through floor grid. Transfer of mice from bright to dark compartment was recorded as transfer latency time (TLT) in seconds. TLT was recorded in control and treated groups ($1^{st}$ Trial, acquisition) and then after 24 hours ($2^{nd}$ Trial, retention). An increase in the TLT on $2^{nd}$ Trial (retention) as compared to $1^{st}$ Trial (acquisition) was taken as the criterion for successful learning and memory (cognitive activity).

Scopolamine induced deficit (Dementia): Scopolamine a muscarinic antagonist, known to produce impairment in cognitive functions (dementia) in human as well as in experimental animals, was used to produce deficit (no significant increase on $2^{nd}$ trial) in passive avoidance learning. Scopolamine was administered 5 min prior to $1^{st}$ trial. Reversal of scopolamine induced deficit i.e. significant increase in $2^{nd}$ trial by test substance indicates potential anti-dementia activity. Scopolamine was administered 5 min prior to $1^{st}$ trial.

Drug administration: Scopolamine was administered 5 min prior to $1^{st}$ trial in test group. Each test compound was administered orally in dose of 20 μmol/kg (1% aq. suspension in gum acacia) 1 hour prior to $2^{nd}$ trial in scopolamine treated mice (n=5). Scopolamine control group received 1 ml/kg of vehicle (1% aq. suspension in gum acacia) orally. Scopolamine was administered 5 min prior to $1^{st}$ trial in test group. Trained control group (n=5) did not receive any drug. Donepezil (10 mg/kg, po, as 1% aqueous suspension in gum acacia) was used as standard drug and given 1 hour prior to $2^{nd}$ trial in scopolamine treated mice.

Statistical analysis: Mean values and standard error (S.E.) of mean were calculated for TLT and specific activity of AChE in the different regions of brain samples of each group. The significance of difference between the values of AChe activity and TLT between the groups was determined by one-way ANOVA test that followed by Dunnett's test.

TABLE 4

Effect of the compounds on scopolamine induced amnesia in passive avoidance test

| Group | $1^{st}$ TRIAL | $2^{nd}$ TRIAL | % Learning | % Improvement in Learning |
|---|---|---|---|---|
| CONTROL | 66.14 | 248 | 274.9 | 0 |
| SCOPOLAMINE | 110 | 147 | 33.6 | 0 |
| SCO + TACRINE | 73.4 | 241 | 228.3 | 194.7 |
| SCO + DONEPEZIL | 91.4 | 245 | 168 | 134.4 |
| SCO + 1b | 99 | 238 | 140.4 | 106.8 |
| SCO + 1c | 89.6 | 230 | 156.7 | 123.09 |
| SCO + 2c | 97 | 195 | 101 | 67.4 |
| SCO + 2h | 92 | 205 | 122.8 | 89.2 |

TABLE 4-continued

Effect of the compounds on scopolamine induced amnesia in passive avoidance test

| Group | $1^{st}$ TRIAL | $2^{nd}$ TRIAL | % Learning | % Improvement in Learning |
|---|---|---|---|---|
| SCO + 2i | 83.5 | 186.4 | 123.2 | 89.6 |
| SCO + 2q | 104 | 218 | 109 | 76 |
| SCO + 2r | 124 | 242 | 95.6 | 62 |

% Learning: $2^{nd}$ Trial – $1^{st}$ trial/1st trial] × 100; % Improvement in Learning: % Learning in treated gp – % Learning in Scopolamine gp The following examples are given by way of illustration and thereof should not be construed to limit the scope of the present invention.

EXAMPLE 1

Hexyl-Carbamic Acid quinolin-6-yl Ester (1a)

(a) Mixture of quinolin-6-ol (0.58 g., 4 mmol), dry dioxane (20 ml), hexyl isocyanate (0.698 ml, 4.8 mmol) and dry pyridine (0.2 ml) was stirred at room temperature (32° C.) for 48 hours. Reaction mixture was concentrated under vaccum, titurated with water (1 ml) and crystallised with ether, to give 1a; yield: 0.80 g. (73.5%), m.p. 89° C., $C_{16}H_{20}N_2O_2$; $^1H$ NMR δ ppm ($CDCl_3$): 0.91 (bs, 3H), 1.33-1.34 (bs, 6H), 1.56-1.62 (m, 2H), 3.24-3.34 (m, 2H), 5.21 (bs, 1H), 7.35-7.42 (m, 1H), 7.48-7.52 (m, 1H), 7.60-7.61 (m, 1H), 8.07-8.12 (m, 2H), 8.86-8.89 (m, 1H); IR $v_{max}$ (KBr) ($cm^{-1}$): 478, 530, 674, 730, 788, 839, 909, 970, 1002, 1040, 1158, 1215, 1258, 1300, 1356, 1462, 1495, 1543, 1709, 1919, 2373, 2861, 2961, 3032, 3286, 3346, 3777, MS: m/z: 273 ($M^+$).

(b) Mixture of quinolin-6-ol (0.58 g., 4 mmol), hexyl isocyanate (0.698 ml, 4.8 mmol) and of dry pyridine (0.3 ml) in dry dioxane (10 ml) was heated at 100° C. with stirring for 3 hours. Reaction mixture was concentrated under vaccum, the residue was titurated with water (1 ml) and crystallised with ether to give 1a; yield: 0.75 g. (68.93%).

(c) Mixture of quinolin-6-ol (0.58 g., 4 mmol), hexyl isocyanate (0.70 ml, 4.8 mmol) and dry pyridine (0.2 ml) in dry dimethylformamide (1 ml) was heated at 50° C. for 5 hours. Reaction mixture was diluted with water (5 ml), extracted with ethyl acetate (2×5 ml) and dried over sodium sulphate. The combined ethyl acetate fractions were concentrated under vaccum and crystallized with ether to give 1a; yield: 0.7 g. (59.7%).

(d) Mixture of quinolin-6-ol (1.16 g., 8 mmol), hexyl isocyanate (1.37 ml, 9.6 mmol) and of dry triethylamine (0.1 ml) in dry dimethylformamide (1 ml) was heated at 50° C. for 5 hours. Reaction mixture was diluted with water (5 ml), extracted with ethyl acetate (2×5 ml), dried over sodium sulphate. The combined ethyl acetate fractions were concentrated under vaccum and crystallized with ether to give 1a, yield: 1.2 g. (55.14%).

EXAMPLE 2

Heptyl-Carbamic Acid quinolin-6-yl ester (1b)

(a) A mixture of quinolin-6-ol (0.29 g., 2 mmol), heptyl isocyanate (0.386 ml 2.4 mmol) and pyridine (1 ml) in dry tetrahydrofuran (10 ml) was heated at 65° C. with stirring for 5 hours. The reaction mixture was cooled and then quenched with water (1 ml), the reaction mixture was concentrated under vaccum and the separated solid was washed with water (2×5 ml) and crystallised with ether to give 1b; yield: 0.25 g. (43.7%), m.p. 78° C., $C_{17}H_{22}N_2O_2$; $^1H$ NMR δ ppm (CDCl$_3$): 0.88 (bs, 3H), 1.33-1.34 (m, 8H), 1.57-1.62 (m, 2H), 3.25-3.35 (m, 2H) 5.10 (s, 1H), 7.36-7.52 (m, 1H), 7.47-7.52 (m, 1H), 7.60-7.61 (m, 1H), 8.07-8.12 (m, 2H), 8.86-8.88 (m, 1H), IR $v_{max}$ (KBr) (cm$^{-1}$) 478, 648, 731, 771, 838, 910, 977, 1024, 1157, 1215, 1363, 1464, 1498, 1532, 1600, 1719, 2371, 2861, 2944, 3022, 3359, 3762; MS: m/z: 287 (M$^+$).

(b) A mixture of quinolin-6-ol (0.29 g., 2 mmol), heptyl isocyanate (0.39 ml, 2.4 mmol) and pyridine (2 ml) in dry tetrahydrofuran (10 ml) was stirred at room temperature (21° C.) for 40 hours, the reaction mixture was concentrated under vaccum and the residue was washed with water (2×5 ml) and crystallized with ether to give 1b; yield: 0.30 g. (52.4%).

(c) A mixture of quinolin-6-ol (0.58 g., 4 mmol), heptyl isocyanate (0.77 ml, 4.8 mmol), potassium carbonate (0.56 g., 4 mmol) and sodium iodide (0.60 g., 4 mmol) in dry dimethylformamide (2 ml) was stirred at 50° C. for 12 hours. The reaction mixture was diluted with water (5 ml), extracted with ethyl acetate (2×5 ml) and chromatographed on silica gel with chloroform as an eluant to give (1b), yield: 0.50 g. (43.7%).

EXAMPLE 3

2-Chloro-phenyl)-carbamic acid quinolin-6-yl ester
(1c)

(a) A mixture of quinolin-6-ol (0.29 g., 2 mmol), 2-chloro-phenyl isocyanate (0.33 ml, 2.4 mmol) and pyridine (0.3 ml) in dry tetrahydrofuran (5 ml) was heated at 65° C. with stirring for 5 hours. The reaction mixture was cooled, quenched with water (1 ml) and concentrated under vaccum. The separated solid was washed with water (2×5 ml) and crystallised with methanol to give 1c; yield: 0.30 g. (50.2%), m.p, 228° C., $C_{16}H_{11}ClN_2O_2$. $^1H$ NMR δ ppm (pyridine d$_5$): 6.96-7.57 (m, 9H), 8.62-8.71 (m, 1H), 9.47 (m, 1H), IR $v_{max}$ (KBr) (cm$^{-1}$): 903, 943, 1040, 1230, 1291, 1353, 1437, 1474, 1552, 1592, 1646, 2373, 3289, 3759.

(b) A mixture of quinolin-6-ol (0.145 g., 1 mmol), 2-chloro-phenyl isocyanate (0.164 ml, 1.2 mmol), potassium carbonate (0.14 g, 1 mmol), potassium iodide (0.16, 1 mmol) g. in dry dimethylformamide (2 ml) was heated at 80° C. for 5 hours. The reaction mixture was diluted with water (5 ml), extracted with ethyl acetate (2×5 ml) and concentrated under vaccum. The residue was washed with methanol (2×2 ml) to give 1e; yield: 0.16 g. (53.6%).

(c) Mixture of quinolin-6-ol (0.29 g., 2 mmol), 2-chloro-phenyl isocyanate (0.33 g., 2.4 mmol), potassium carbonate (0.28 g., 2 mmol) and potassium iodide (0.32 g., 2 mmol) in dry dioxane (10 ml) was heated at 100° C. with stirring for 4 hours. Reaction mixture was concentrated under vaccum, diluted with water, extracted with ethyl acetate (2×5 ml) and concentrated under vaccum. Residue was washed with methanol (2×3 ml) to give 1c; yield: 0.30 g. (50.2%).

EXAMPLE 4

(3-bromo-phenyl)-carbamic acid quinolin-6-yl ester
(1d)

(a) A solution of quinolin-6-ol (0.29 g., 2 mmol) in dry dimethylformamide (3 ml) was added to a stirred suspension of sodium hydride (0.048 g., 2 mmol) in dry dimethylformamide (2 ml) at −10° C. during 5 min. The reaction mixture was stirred for ½ hours. Then 3-bromo-phenyl isocyanate (0.475 g., 2.4 mmol) was added to the stirring reaction mixture. Stirring was continued for additional 1 hr. during which the temperature was allowed to rise to room temperature (21° C.). The reaction mixture was quenched with water (0.2 ml), diluted with water (2 ml), extracted with ethyl acetate (2×5 ml) and dried over sodium sulphate. The combined fractions of ethyl acetate were concentrated under vaccum. The residue was washed with methanol (2×2 ml) to give 1d; yield: 0.35 g. (51.01%), m.p. 260° C., $C_{16}H_{11}BrN_2O_2$; $^1H$ NMR δ ppm (pyridine d$_5$): 7.09-7.58 (m, 9H), 8.28 (bs, 2H), 9.58 (bs, 1H); IR $v_{max}$ (KBr) (cm$^{-1}$). 522, 645, 743, 782, 877, 928, 992, 1069, 1227, 1286, 1406, 1470, 1581, 1637, 1875, 1946, 2374, 3290, 3753, 3872, 3952.

(b) A mixture of quinolin-6-ol (0.29 g, 2 mmol), 3-bromo-phenyl isocyanate (0.47 g., 2.4 mmol), potassium carbonate 0.28 g. (0.28 g. 2 mmol) and potassium iodide (0.32 g.) in dry dimethylformamide (2 ml) was heated at 80° C. for 20 hours. The reaction mixture was diluted with water (5 ml), extracted with ethyl acetate (2×5 ml) and dried over sodium sulphate. The combined ethyl acetate fractions were concentrated under vaccum. The residue was washed with methanol (2×3 ml) to give 1d, yield: 0.34 g. (49.5%).

EXAMPLE 5

Hexyl-carbamic acid 1, 2, 3, 4tetrahydroquinolin-6-yl ester (2a)

A mixture of hexyl-carbamic acid 1-benzyl-1, 2, 3, 4-tetrahydro-quinolin-6-yl ester (0.732 g., 2 mmol) and 5% Pd—C (0.08 g.) in absolute ethanol (20 ml) was shaken in a par apparatus at room temperature (38° C.) under 50 psi pressure of hydrogen for 4 hours. Pd—C was then discarded through filtration. The reaction mixture was concentrated under vaccum and the separated solid was washed with chloroform (2×5 ml) to give 2a; yield: 0.60 g. (64.1%), m.p.: 100° C., $C_{16}H_{24}N_2O_2$; $^1H$ NMR δ ppm (CDCl$_3$): 0.88 (bs, 3H), 1.25-1.30 (m, 5H), 1.51-1.58 (m, 3H), 1.85-1.97 (m, 3H), 2.74 (t, 2H), 3.16-3.29 (m, 4H), 3.6 (bs, 1H), 4.87 (bs, 1H), 6.39-6.4 (m, 1H), 6.68-6.71 (m, 2H), IR $v_{max}$ (KBr) (cm$^{-1}$): 770, 816, 886, 956, 1006, 1101, 1152, 1221, 1243, 1311, 1354, 1505, 1626, 1702, 1848, 2372, 2856, 2929, 3392, 3760, 3809, 7874, MS: m/z: 277 (M$^+$).

EXAMPLE 6

Heptyl-carbamic acid 1, 2, 3, 4-tetrahydro-quinolin-6-yl ester (2b)

(a) A nitrogen flushed mixture of heptyl-carbamic acid 1-benzyl-1, 2, 3, 4-tetrahydro-quinolin-6-yl ester (0.378 g., 1 mmol) and 10% Pd—C (0.02 g.) in absolute ethanol (20 ml) was shaken in a par apparatus at room temperature (38° C.) under 55 psi pressure of hydrogen for 4 hours. Pd—C was then discarded through filtration. The reaction mixture was concentrated under reduced pressure and the residue was chromatographed with methanol: dichloromethane (1:99) to give 2b; yield: 0.25 g. (84.6%), m.p.: 67° C., $C_{17}H_{26}N_2O_2$; $^1H$ NMR δ ppm (CDCl$_3$): 0.88 (bs, 3H), 1.20-1.30 (m, 7H, 1.56 (bs, 3H), 1.88-1.93 (m, 2H), 2.74 (t, 2H), 3.23-3.28 (m, 4H), 3.66-3.76 (m, 1H), 4.89 (bs, 1H), 6.40-6.44 (m, 1H), 6.68-6.71 (m, 2H); IR $v_{max}$ (KBr) (cm$^{-1}$): 561, 665, 768, 815, 887, 976, 1149, 1223, 1308, 1353, 1506, 1621, 1699, 2362, 2857, 2930, 3763.

(b) Ni—Al alloy (0.098 g.) was added portionwise during 1 min. to stirring mixture of heptyl-carbamic acid quinolia-6-yl ester (0.145 g.), 10% potassium hydroxide in water (3.54 ml) and ethanol (10 ml) at 0-4° C. The reaction mixture was continued to stir for additional 2.5 hours while the temperature of the reaction mixture was maintained at 50° C. The reaction mixture was filtered, Ni—Al alloy was discarded through filtration, and the filtrate was concentrated under vaccum. The residue so obtained was crystallized with methanol (or acetone) to give 2b; yield: 0.10 g. (67.7%).

EXAMPLE 7

(3-Bromo-phenyl)-carbamic acid 1,2,3,4-tetrahydro-quinolin-6-yl ester (2c)

A nitrogen flushed mixture of 3-bromo-phenyl -carbamic acid 1-benzyl-1, 2, 3, 4-tetrahydro-quinolin-6-yl ester (0.218 g., ½ mmol) and 5% Pd—C (0.02 g.) in absolute ethanol (25 ml) was shaken in a par apparatus at room temperature (38° C.) under 50 psi pressure of hydrogen for 4 hours. Pd—C was then discarded through filtration. The reaction mixture was concentrated under reduced pressure and the residue was washed with dichloromethane (2×3 ml) to give 2c; yield: 0.16 g. (92.4%), m.p.: 198° C., $C_{16}H_{15}BrN_2O_2$, $^1$H NMR δ ppm (CDCl$_3$+DMSO-d$_6$): 1.73-1.81 (m, 2H), 2.55 (t, 2H), 3.06 (t, 2H), 6.67-6.98 (m, 4H), 6.90-7.20 (m, 2H), 7.36 (bs, 1H), 9.39 (bs, 1H), IR $v_{max}$ (KBr) (cm$^{-1}$): 509, 694, 758, 815, 886, 1012, 1084, 1149, 1216, 1319, 1352, 1442, 1504, 1549, 1600, 1710, 2365, 2479, 2727, 2827, 2927, 3420, 3780.

EXAMPLE 8

(2-Chloro-phenyl)-carbamic acid 1, 2, 3, 4-tetrahydro-quinolin-6-yl ester (2d)

A nitrogen flushed mixture of 3-chloro-phenyl -carbamic acid 1-benzyl-1, 2, 3, 4-tetrahydro-quinolin-6-yl ester (0.196 g., ½ mmol) and 5% Pd—C (0.02 g.) in absolute ethanol (25 ml) was shaken in a par apparatus at room temperature (40° C.) under 50 psi pressure of hydrogen for 5 hours. Then Pd—C was discarded through filtration. The reaction mixture was concentrated under reduced pressure and the residue was washed with dichloromethane (2×3 ml) to give 2d; yield: 0.11 g. (72.8%), m.p.: 201° C., $C_{16}H_{15}ClN_2O_2$; $^1$H NMR δ ppm (CD$_3$OD): 2.00-2.12 (m, 2H), 2.88 (t, 2H), 3.44 (t, 2H), 6.97-7.41 (m, 7H); IR $v_{max}$ (KBr) (cm$^{-1}$): 509, 609, 699, 753, 814, 857, 887, 9297, 1006, 1064, 1207, 1316, 1351, 1386, 1441, 1501, 1600, 1748, 1960, 2484, 2645, 2725, 2830, 2889, 3134, 3251, 3416.

EXAMPLE 9

(4Chloro-3-trifluoromethyl-phenyl)-carbamic acid 1, 2, 3, 4tetrahydro-quinolin-6-yl ester (2e)

A nitrogen flushed mixture of 4-chloro-3-trifluoromethyl-phenyl-carbamic acid 1-benzyl-1, 2, 3, 4-tetrahydro-quinolin-6-yl ester (0.23 g. ½ mmol) and 5% Pd—C (0.02 g.) in absolute ethanol (20 ml) was shaken in a par apparatus at room temperature (38° C.) under 50 psi pressure of hydrogen for 5 hours. Pd—C was then discarded through filtration. The reaction mixture was concentrated under reduced pressure and the residue was washed dichloromethane (2×3 ml) to give 2e; yield: 0.16 g. (86.4%), m.p.: 150° C., $C_{17}H_{14}ClF_3N_2O_2$; $^1$H NMR δ ppm (DMSO-d$_6$): 1.89-1.95 (m, 2H.), 2.76 (t, 2H), 3.28 (t, 2H), 6.44-6.49 (m, 1H), 6.72-6.75 (m, 2H), 7.37-8.0 (m, 2H),10.14 (bs, 1H); IR $v_{max}$ (KBr) (cm$^{-1}$): 661, 698, 769, 796, 819, 892, 944, 1023, 1072, 1147, 1217, 1290, 1347, 1384, 1424, 1450, 1506, 1599, 1707, 1740, 2364, 2489, 2837, 2950, 3359, 3773, 3888.

EXAMPLE 10

(4bromo-phenyl)-carbamic acid 1,2,3,4-tetrahydro-quinolin-6-yl ester (2f)

Nitrogen flushed mixture of 4-bromo-phenyl-carbamic acid 1-benzyl-1,2,3,4-tetrahydro-quinolin-6-yl ester (0.655 g., 1.5 mmol) and 5% Pd—C (0.06 g.) in absolute ethanol (20 ml) was shaken in a par apparatus at room temperature (40° C.) under 50 psi pressure of hydrogen for 5 hours. Then Pd—C was discarded through filtration. The reaction mixture was concentrated under reduced pressure and the residue was washed with dichloromethane (2×3ml) to give 2f; yield: 0.48 g. (92.3%), m.p: 198° C., $C_{16}H_{15}BrN_2O_2$; $^1$H NMR δ ppm (DMSO): 1.82-2.00 (bs, 2H), 2.76 (t, 2H), 3.27 (t, 2H), 7.01-7.08 (m, 3H), 7.25-7.39 (m, 4H), 10.14 (s, 1H), IR $v_{max}$ (KBr) (cm$^{-1}$): 506, 608, 690, 749, 814, 884, 927, 1005, 1211, 1265, 1319, 1354, 1401, 1440, 1501, 1550, 1601, 1748, 1938, 2370, 2779, 2725, 2767, 2823, 2922, 3262, 3420, 3774.

EXAMPLE 11

(a) Heptyl-carbamic acid 1-benzyl-1,2,3,4tetrahydro-quinolin-6-yl ester (2 g)

Mixture of 1-benzyl-1, 2, 3, 4-tetrahydro-quinolin-6-ol (0.239 g., 1 mmol), heptyl isocyanate (0.169 g., 1.2 mmol) and pyridine (1 ml) in dry tetrahydrofuran (10 ml), was heated with stirring at 65° C. for 48 hours. Reaction mixture was quenched with water (1 ml) and concentrated under vaccum. The separated solid was washed with water (2×5 ml) and crystallised with ether to give (2 g) as oil; yield: 0.200 g. (52.6%), $C_{24}H_{32}N_2O_2$; $^1$H NMR δ ppm (CDCl$_3$): 0.86 (bs, 3H), 1.20-1.29 (m, 6H), 1.55-1.58 (m, 4H), 1.96-2.06 (m, 2H), 2.79 (t, 2H), 3.17-3.36 (m, 4H), 4.44 (st, 2H), 4.87 (bs, 1H), 6.39-6.44 (m, 1H$_4$), 6.71-6.75 (m, 2M), 7.25-7.34 (m, 5H); IR $v_{max}$ (Neat) (cm$^{-1}$): 757, 902, 1.70, 1160, 1199, 1228, 1348, 1458, 1502, 1618, 1718, 2362, 2857, 2928, 3028, 3342, 3854; MS: m/z=380 (M$^+$).

(b) A mixture of 1-benzyl-1, 2, 3, 4-tetrahydro-quinolin-6-ol (0.239 g., 1 mmol), heptyl isocyanate (0.169 ml, 1.2 mmol) and pyridine (2 ml) in dry dichloromethane (10 ml) was heated with stirring at 45° C. with stirring for 100 hours. The reaction mixture was cooled, washed with water (3×5 ml) and dried over sodium sulphate. The reaction mixture was concentrated under vaccum. The residue so obtained was chromatographed on silica gel using dichloromethane: hexane (25:75) as eluant to give 2 g; yield: 0.090 g. (39.03%).

EXAMPLE 12

Hexyl-carbamic acid 1-benzyl-1, 2, 3, 4-tetrahydro-quinolin-6-yl ester (2 h)

Mixture of 1-benzyl-1,2,3,4-tetrahydro-quinolin-6-ol (0.239 g., 1 mmol), hexyl isocyanate (0.152 g., 1.2 mmol) and pyridine (0.5 ml) in dry ThF (10 ml) was heated with stirring at 65° C. for 72 hours. Reaction mixture was cooled, quenched with water (1 ml) and concentrated under vaccum. Separated solid was washed with water (2×3 ml) and crystallised with ether to give 2 h, yield: 0.30 g. (81.9%), m.p. >335, $C_{23}H_{30}N_2O_2$, $^1$H NMR δ ppm (CDCl$_3$): 0.89 (bs, 3H), 0.90-1.29 (m, 4H), 1.50-1.56 (m, 4H), 1.98-2.15 (m, 2H), 2.79 (t, 2H), 3.17-3.36 (m, 4H), 4.44 (s, 2H), 4.88 (bs, 1H), 6.42 (d, 1H), 6.67-6.75 (m, 2H), 7.22-7.35 (m, 5H); IR $v_{max}$ (KBr) (cm$^{-1}$): 669, 760, 1026, 1217, 1348, 1501, 1615, 1728, 2402, 2857, 3018, 3450.

(b) Mixture of 1-benzyl-1,2,3,4-tetrahydro-quinolin-6-ol (0.239 g., 1 mmol), hexyl isocyanate (0.174 ml, 1.2 mmol) and triethylamine (1 ml) in dry chloroform (10 ml) was heated with stirring for 48 hours. The reaction mixture was cooled, washed with water (2×5 ml), dried over sodium sulphate and concentrated under vaccum. The residue so obtained was chromatographed with 20:80 chloroform:hexane as eluant to give 2 h; yield. 0.25 g. (68.3%).

EXAMPLE 13

(2-Chloro-phenyl)carbamic acid 1-benzyl-1, 2, 3, 4-tetrahydro-quinolin-6 yl ester (2i)

(a) A solution of 1-benzyl-1, 2, 3, 4-tetrahydro-quinolin-6-ol (0.239 g., 1 mmol) in dry tetrahydrofuran (5 ml) was added to a stirred suspension of sodium hydride (0.024 g, 1 mmol) in dry tetrahydrofuran (5 ml) at −10° C. during 5 min. The reaction mixture was stirred for 20 min. Then 2-chlorophenyl isocyanate was added (0.184 g., 1.2 mmol) was added to the stirring reaction mixture. Stirring was continued for additional 2.5 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using chloroform: hexane (20:80) as eluant to give 2i; yield: 0.20 g. (50.9%), m.p. 130° C., $C_{23}H_{21}ClN_2O_2$; $^1$H NMR δ ppm (CDCl$_3$): 1.90-2.02 (m, 2H), 2.82 (t, 2H), 3.30-3.35 (m, 2H), 4.46 (s, 2H), 6.43-6.48 (m, 1H), 6.74-6.82 (m, 2H), 7.20-7.25 (m, 5H), 7.44-7.46 (m, 4H); IR $v_{max}$ (KBr) (cm$^{-1}$): 534, 754, 807, 882, 1018, 1059, 1193, 1245, 1303, 1352, 1432, 1506, 1597, 1718, 1749, 2371, 2830, 2922, 3418, 3760.

(b) A solution of 1-benzyl-1, 2, 3, 4-tetrahydro-quinolin-6-ol (0.239 g., 1 mmol) in dry ether (10 ml) was added to a stirred suspension of sodium hydride (0.024 g., 1 mmol) in dry ether (15 ml) at −10° C. during 10 min. The reaction mixture was stirred for 20 min. Then 2-chlorophenyl isocyanate (0.184 g:, 1.2 mmol) was added to the stirring reaction mixture. Stirring was continued for additional 2 hours during which the temperature was allowed to rise to room temperature (35° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using chloroform: hexane (20:80) as eluant to give 2i; yield: 0.25 g. (63.7%).

EXAMPLE 14

(3bromo-phenyl)-carbamic acid 1-benzyl-1, 2, 3, 4tetrahydro-quinolin-6-yl ester (2j)

A solution of 1-benzyl-1, 2, 3, 4-tetrahydro-quinolin-6-ol (0.239 g., 1 mmol) in dry tetrahydrofuran (5 ml) was added to a stirred suspension of sodium hydride (0.024 g. 1 mmol) in dry tetrahydrofuran (5 ml) at −10° C. during 5 min. The reaction mixture was stirred for 20 min. Then 3-bromo-phenyl isocyanate (0.237 g., 1.2 mmol) was added to the stirring reaction mixture. Stirring was continued for additional 2.5 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using chloroform: hexane (20:80) as eluant to give 2j; yield: 0.25 g. (57.2%), m.p. 117° C., $C_{23}H_{21}BrN_2O_2$; $^1$H NMR δ ppm (CDCl$_3$): 2.00-2.20 (m, 2H), 2.81 (t, 2H), 3.36 (t, 2H), 4.46 (s, 21), 6.46 (d, 1H), 6.79-6.81 (m, 2H), 7.19-7.31 (m, 8H), 7.69 (s, 1H); IR $v_{max}$ (KBr) (cm$^{-1}$): 621, 670, 759, 885, 930, 1021, 1117, 1215, 1348, 1420, 1505, 1594, 1743, 2369, 2855, 2928, 3021, 3428; MS: m/z=437 (M$^+$).

EXAMPLE 15

(4-Chloro-3-trifluoromethyl-phenyl)-carbamic acid 1-benzyl-1, 2, 3, 4-tetrahydro-quinolin-6-yl ester (2k)

(a) A solution of 1-benzyl-1, 2, 3, 4-tetrahydro-quinolin-6-ol (0.239 g., 1 mmol) in dry tetrahydrofuran (5 ml) was added to a stirred suspension of sodium hydride (0.024 g., 1 mmol) in dry tetrahydrofuran (5 ml) at −10° C. during 5 min. The reaction mixture was stirred for 20 min. Then 4-chloro-3-trifluoromethyl-phenyl isocyanate (0.265 g., 1 mmol) was added to the stirring reaction mixture. Stirring was continued for additional 2.5 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using chloroform-hexane (20:80) as eluant to give 2k; yield: 0.25 g. (54.2%), m.p. 151° C., $C_{24}H_{20}ClF_3N_2O_2$; $^1$H NMR δ ppm (CDCl$_3$): 2.00 (bs, 2H), 2.79 (t, 2H), 3.36 (t, 2H), 4.46 (s, 2H), 6.42-6.46 (m, 1H), 6.70-6.79 (m, 2H), 6.96 (s, 1H), 7.23-7.31 (m, 5H), 7.75-7.82 (m, 2H); IR $v_{max}$ (KBr) (cm$^{-1}$): 555, 701, 898, 1027, 1218, 1362, 1509, 1635, 1721, 2375, 2658, 2957, 3028, 3449, 3756; MS: m/z=461 (M$^+$).

(b) A mixture of 1-benzyl-1, 2, 3, 4-tetrahydro-quinolin-6-ol (0.24 g., 1 mmol), 4-chloro-3-trifluoromethyl-phenyl isocyanate (0.265 g., 1 mmol), pulverized sodium hydroxide (0.044 g., 1 mmol) in dry tetrahydrofuran (20 ml) was stirred for 14 hours at room temperature (35° C.). The reaction mixture was concentrated under vaccum, diluted with water, extracted with chloroform and concentrated under vaccum. The residue was then chromatographed on silica gel using chloroform-hexane (30.70) as eluant to give 2k; yield: 0.20 g. (43.4%).

EXAMPLE 16

(4-bromophenyl)carbamic acid 1-benzyl-1, 2, 3, 4-tetrahydro-quinolin-6-yl ester (2l)

(a) A solution of 1-benzyl-1, 2, 3, 4-tetrahydro-quinolin-6-ol (0.239 g., 1 mmol) in dry tetrahydrofuran (5 ml) was added to a stirred suspension of sodium hydride (0.024 g., 1 mmol) in dry tetrahydrofuran (5 ml) at −10° C. during 5 min, The reaction mixture was stirred for 20 min. Then 4-bromo-phenyl isocyanate (0.237 S., 1.2 mmol)) was added to the stirring reaction mixture. Stirring was continued for additional 2.5 hours during which the temperature was allowed to rise to room temperature (35° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vacuum. The residue was chromatographed on silica gel using (20:80) chloroform: hexane as eluant to give 2l; yield: 0.26 g. (59.4%), m.p. 170° C.; $C_{23}H_{21}BrN_2O_2$; $^1H$ NMR δ ppm (CDCl$_3$): 2.00 (bs, 2H), 2.81 (t, 2H), 3.36 (t, 2H), 4.46 (s, 2H), 6.44 (d, 1H), 6.79-6.81 (m, 2H), 7.26-7.45 (m, 9H). IR $v_{max}$ (KBr) (cm$^{-1}$): 501, 694, 765, 813, 1010, 1070, 1219, 1352, 1505, 1599, 1716, 2225, 2375, 2830, 2934, 3330, 3757; MS: m/z=437 (M$^+$).

(b) A mixture of 1-benzyl-1, 2, 3, 4-tetrahydro-quinolin-6-ol (0.239 g., 1 mmol), 4-chloro-3-trifluoromethyl-phenyl isocyanate (0.237 g., 1 mmol), pulverized potassium hydroxide (0.057 g., 1 mmol) in dry dimethylformamide (2 ml) was stirred for 12 hours at room temperature (35° C.). The reaction mixture was diluted with water (5 ml), extracted with ethyl acetate (3×5 ml), dried over sodium sulphate and the combined ethyl acetate fractions were concentrated under vaccum. The residue was then chromatographed on silica gel using dichloromethane: hexane (20:80) as eluant to give 2l; yield: 0.18 g. (41.2%).

EXAMPLE 17

Hexyl-carbamic acid 1-methyl-1, 2, 3, 4-tetrahydro-quinolin-6-yl ester (2m)

(a) A solution of 1-methyl-1, 2, 3, 4-tetrahydro-quinolin-6-ol (0.244 g., 1 mmol) in dry tetrahydrofuran (5 ml) was added to a stirred suspension of sodium hydride (0.024 g., 1 mmol) in dry tetrahydrofuran (5 ml) at –10° C. during 5 min. The reaction mixture was stirred for 20 min. Then hexyl isocyanate (0.26 g., 1 mmol) was added to the stirring reaction mixture. Stirring was continued for additional 2.5 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using chloroform: hexane (20.80) as eluant to give 2m; yield: 0.25 g. (57.9%), m.p. 50° C., $C_{17}H_{26}N_2O_2$; $^1H$ NMR δ ppm (CDCl$_3$): 0.88 (bs, 3H), 1.26-1.54 (m, 8H), 1.96-1.99 (m, 2H), 2.71 (t, 2H), 2.85 (s, 3H), 3.14-3.25 (m, 4H), 4.90 (bs, 1H), 6.54 (d, 1H), 6.71-6.87 (m, 2H); IR $v_{max}$ (KBr) (cm$^{-1}$): 656, 757, 895, 1160, 1226, 1319, 1387, 1502, 1721, 2932, 1914, 2370, 2863, 3339, 3773; MS: m/z: 391 (M$^+$).

(b) A solution of hexyl-carbamic acid-1, 2, 3, 4-tetrahydro-quinolin-6-yl ester (0.276 g., 1 mmol) in dry tetrahydrofuran (5 ml) was added to a stirred suspension of sodium hydride (0.024 g., 1 mmol) in dry tetrahydrofuran (5 ml) at –10° C. during 5 min. The reaction mixture was stirred for 20 min. Then methyl iodide (0.224 ml, 3.6 mmol) was added to the stirring reaction mixture. Stirring was continued for additional 1.25 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using chloroform: hexane (30:70) as eluant to give 2m; yield: 0.15 g. (51.7%).

EXAMPLE 18

Heptyl-carbamic acid 1-methyl-1,2,3,4-tetrahydroquinolin-6-yl ester (2n)

(a) A solution of 1-methyl-1, 2, 3, 4-tetrahydro-quinolin-6-ol (0.490 g., 3 mmol) in dry dimethylformamide (5 ml) was added to a stirred suspension of sodium hydride (0.072 g., 3 mmol) in dry dimethylformamide (5 ml) at –10° C. during 5 min. The reaction mixture was stirred for 20 min. Then heptyl isocyanate (0.58 g., 3 mmol) was added to the stirring reaction mixture. Stirring was continued for additional 2.5 hours during which the temperature was allowed to rise to room temperature (37° C.). The reaction mixture was quenched with water (0.2 ml), diluted with water (5 ml), extracted with ethyl acetate (2×5 ml) and dried over sodium sulphate. The combined fractions of ethyl acetate were concentrated under vaccum. The residue was chromatographed on silica gel using chloroform: hexane (20:80) as eluant to give 2n; yield: 0.60 g. (65.6%), m.p. 60° C., $C_{18}H_{28}N_2O_2$; $^1$NMR δ ppm (CDCl$_3$): 0.88 (bs, 3H), 1.30-1.56 (m, 10H), 1.95-2.05 (m, 2H), 2.68 (t, 2H), 2.86 (s, 3H), 3.15-3.26 (m, 4H), 6.52 (d, 1H), 6.70-6.86 (m, 2H); IR $v_{max}$ (KBr) (cm$^{-1}$) 758, 899, 1160, 1226, 1318, 1390, 1503, 1621, 1718, 2861, 2930, 3348, 3759, MS: m/z: 305 (M$^+$).

(b) A mixture of heptyl-carbamic acid-1, 2, 3, 4-tetrahydro-quinolin-6-yl ester (0.58 g., 2 mmol), methyl iodide (0.224 ml, 3.6 mmol) and pulverized potassium hydroxide (0.16 g., 2 mmol) in dry tetrahydrofuran (10 ml) was stirred for 5 hours at room temperature (36° C.). The reaction mixture was concentrated under vaccum, diluted with water (5 ml), extracted with ether (3×5 ml), dried over sodium sulphate and the combined ether fractions were concentrated under vaccum. The residue was then chromatographed on deactivated silica gel (water: silica gel=12.88, v/w) using dichloromethane: hexane (20:80) as eluant to give 2n; yield: 0.36 g. (59.2%).

EXAMPLE 19

(2-Chloro-phenyl)-carbamic acid 1-methyl-1, 2, 3, 4-tetrahydro-quinolin-6-yl ester (2o)

(a) A solution of 1-methyl-1, 2, 3, 4-tetrahydro-quinolin-6-ol (0.326 g., 2 mmol) in dry dimethylformamide (5 ml) was added to a stirred suspension of sodium hydride (0.048 g., 2 mmol) in dry dimethylformamide (5 ml) at –10° C. during 5 min. The reaction mixture was stirred for 30 min. Then 2-chloro-phenyl isocyanate (0.329 g., 2 mmol) was added to the stirring reaction mixture. Stirring was continued for additional 2.5 hours during which the temperature was allowed to rise to room temperature (35° C.). The reaction mixture was quenched with water (0.2 ml), diluted with water (5 ml), extracted with ethyl acetate (2×5 ml) and dried over sodium sulphate. The combined fractions of ethyl acetate were concentrated under vaccum. The residue was chromatographed on silica gel using chloroform: hexane (20:80) as eluant to give 2o; yield: 0.50 g. (78.9%), m p. 120° C., $C_{17}H_{17}ClN_2O_2$; $^1H$ NMR δ ppm (CDCl$_3$); 1.95-2.01 (m, 2H), 2.77 (t, 2H), 2.88 (s, 3H), 3.21 (t, 2H), 6.54-6.58 (m, 1H), 6.81-7.05 (m, 3l), 7.23-7.44 (m, 2H), 8.18-8.22 (m, 1H); IR $v_{max}$ (KBr) (cm$^{-1}$); 563, 670, 758, 1017, 1201, 1305, 1432, 1507, 1596, 1746, 2375, 2940, 3020, 3282, 3413, 3686, 3763.

(b) A solution of 1 of 2-chloro-phenyl -carbamic acid-1, 2, 3, 4-tetrahydro-quinolin-6-yl ester (0.302 g., 1.5 mmol) in dry dioxane (5 ml) was added to a stirred suspension of sodium hydride (0.036 g., 1.5 mmol) in dry dioxane (5 ml) at −10° C. during 5 min. The reaction mixture was stirred for 20 min. Then methyl iodide (0.122 ml, 1.8 mmol) was added to the stirring reaction mixture. Stirring was continued for additional 1.5 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using 30:70 chloroform:hexane (30:70) as eluant to give 2o; yield: 0.50 g. (47.5%).

EXAMPLE 20

(3bromo-phenyl)-carbamic acid 1-methyl-1, 2, 3, 4tetrahydroquinolin-6-yl ester (2p)

(a) A solution of 1-methyl-1, 2, 3, 4-tetrahydro-quinolin-6-ol (0.326 g., 2 mmol) in dry tetrahydrofuran (5 ml) was added to a stirred suspension of sodium hydride (0.048 g., 2 mmol) in dry tetrahydrofuran (5 ml) at −10° C. during 5 min. The reaction mixture was stirred for 30 min. Then 2-bromo-phenyl isocyanate (0.30 g., 2.4 mmol) was added to the stirring reaction mixture. Stirring was continued for additional 1.5 hours during which the temperature was allowed to rise to room temperature (35° C.). The reaction mixture was quenched with water (0.2 ml), concentrated under vaccum, diluted with water (5 ml), extracted with ethyl acetate (2×5 ml) and dried over sodium sulphate. The combined fractions of ethyl acetate were concentrated under vaccum. The residue was chromatography on silica gel using chloroform: hexane (20:80) as eluant to give 2p; yield: 0.59 g. (81.7%), m.p. −10° C., $C_{17}H_{17}BrN_2O_2$; $^1H$ NMR δ ppm (CDCl$_3$): 1.94-2.00 (m, 2H), 2.77 (t, 2H), 2.87 (s, 3H), 3.20 (t, 2H), 6.53-6.57 (m, 1H), 6.78-6.87 (m, 2H), 7.17-7.79 (m, 4H); IR $v_{max}$ (KBr) (cm$^{-1}$): 595, 674, 774, 883, 1004, 1194, 1411, 1479, 1270, 1595, 1742, 2382, 2927, 3431, 3689, 3774.

EXAMPLE 21

(4-Chloro-3-trifluoromethyl-phenyl)-carbamic acid 1-methyl-1,2,3,4-tetrahydro-quinolin-6-yl ester (2q)

(a) A solution of 1-methyl-1, 2, 3, 4-tetrahydro-quinolin-6-ol (0.326 g., 2 mmol) in dry tetrahydrofuran (5 ml) was added to a stirred suspension of sodium hydride (0.048 g., 2 mmol) in dry tetrahydrofuran (5 ml) at −10° C. during 5 min. The reaction mixture was stirred for 30 min. Then 2-chloro-phenyl isocyanate (0.53, 2 mmol) was added to the stirring reaction mixture, Stirring was continued for additional 2.5 hours during which the temperature was allowed to rise to room temperature (34° C.). The reaction mixture was quenched with water (0.2 ml), concentrated under vaccum, diluted with water (5 ml), extracted with ethyl acetate (2×5 ml) and dried over sodium sulphate. The combined fractions of ethyl acetate were concentrated under vaccum residue was chromatographed on silica gel using chloroform hexane (20:80) as eluant to give 2q; yield: 0.52 g. (67.6%), m.p. 152° C., $C_{18}H_{16}ClF_3N_2O_2$; $^1H$ NMR δ ppm (CDCl$_3$): 1.94-2.00 (m, 2H), 2.76 (t, 2H), 2.87 (s, 3H), 3.20 (t, 2H), 6.52-6.57 (m, 1H), 6.78-6.82 (m, 2H), 7.46-7.81 (m, 3H); IR $v_{max}$ (KBr) (cm$^{-1}$): 537, 666, 756, 831, 894, 1029, 1147, 1264, 1423, 1489, 1542, 1596, 1698, 1741, 2373, 2928, 3118, 3232, 3402, 3687, 3760, MS: m/z: 385 (M$^+$).

(b) A solution of 1 of (4-chloro-3-trifluoromethyl-phenyl)-carbamic acid -1,2,3,4-tetrahydro-quinolin-6-yl ester (0.74 g., 2 mmol) in dry dimethylformamide (5 ml) was added to a stirred suspension of sodium hydride (0.048 g., 2 mmol) in dry dimethylformamide (5 ml) at −10° C. during 5 min. The reaction mixture was stirred for 30 min. Then methyl iodide (0.224 ml, 3.6 mmol) was added to the stirring reaction mixture. Stirring was continued for additional 1.25 hours during which the temperature was allowed to rise to room temperature (34° C.). The reaction mixture was quenched with water (0.2 ml), concentrated under vaccum, diluted with water (5 ml), extracted with chloroform (2×5 ml) and dried over sodium sulphate. The combined fractions of chloroform were concentrated under vaccum. The residue was chromatographed on silica gel using dichloromethane-hexane (20:80) as eluant to give 2q; yield: 0.42 g. (54.6%).

EXAMPLE 22

(4-bromophenyl)carbamic acid 1-methyl-1, 2, 3, 4-tetrahydroquinolin-6-yl ester (2r)

(a) A solution of 1-methyl-1, 2, 3, 4-tetrahydro-quinolin-6-ol (0.326 g., 2 mmol) in dry tetrahydrofuran (5 ml) was added to a stirred suspension of sodium hydride (0.048 g., 2 mmol) in dry tetrahydrofuran (5 ml) at −10° C. during 5 min. The reaction mixture was stirred for 30 min. Then 2-bromo-phenyl isocyanate (0.734, 2 mmol) was added to the stirring reaction mixture. Stirring was continued for additional 2.5 hours during which the temperature was allowed to rise to room temperature (34° C.). The reaction mixture was quenched with water (0.2 ml), concentrated under vaccum, diluted with water (5 ml), extracted with ethyl acetate (2×5 ml) and dried over sodium sulphate. The combined fractions of ethyl acetate were concentrated under vaccum. The residue was chromatographed on silica gel using chloroform hexane (20:80) as eluant to give 2r; yield: 0.40 g. (52.3%), m.p. 155° C., $C_{17}H_{17}BrN_2O_2$; $^1H$ NMR δ ppm (CDCl$_3$): 1.94-2.03 (m, 2H), 2.76 (t, 2H), 2.87 (s, 3H), 3.20 (t, 2H), 6.52-6.57 (m, 1H), 6.78-6.88 (m, 2H), 7.25-7.45 (m, 4H); IR $v_{max}$ (KBr) (cm$^{-1}$): 674, 774, 1020, 1365, 1590, 2366, 2834, 2934, 3433, 3757, 3867, 3906; MS: m/z: 361 (M$^+$).

We claim:

1. A substituted carbamic acid quinolinyl ester is selected from the group consisting of:
   - 1a. hexyl-carbamic acid quinolin-6-yl ester
   - 1b. heptyl-carbamic acid quinolin-6-yl ester
   - 1c. (2-chloro-phenyl)-carbamic acid quinolin-6-yl ester
   - 1d. (3-bromo-phenyl)-carbamic acid quinolin-6-yl ester
   - 2a. hexyl-carbamic acid 1, 2, 3, 4-tetrahydro-quinolin-6-yl ester
   - 2b. heptyl-carbamic acid 1, 2, 3, .sup.4-tetrahydro-quinolin-6-yl ester
   - 2c. (3-bromo-phenyl)-carbamic acid 1,2,3,4-tetrahydro-quinolin-6-yl ester
   - 2d. (2-chloro-phenyl)-carbamic acid 1, 2, 3, 4-tetrahydro-quinolin-6-yl ester
   - 2e. (4-chloro-3-trifluoromethyl-phenyl)-carbamic acid 1, 2, 3, 4-tetrahydro-quinolin-6-yl ester
   - 2f. (4-bromo-phenyl)-carbamic acid 1, 2, 3, 4-tetrahydro-quinolin-6-yl ester
   - 2g. heptyl-carbamic acid 1-benzyl-1, 2, 3, 4-tetrahydro-quinolin-6-yl ester
   - 2h. hexyl-carbamic acid 1-benzyl-1, 2, 3, 4-tetrahydro-quinolin-6-yl ester
   - 2i. (2-chloro-phenyl)-carbamic acid 1-benzyl-1, 2, 3, 4-tetrahydro-quinolin-6-yl ester
   - 2j. (3-bromo-phenyl)-carbamic acid 1-benzyl-1, 2, 3, 4-tetrahydro-quinolin-6-yl ester 2k. (4-chloro-3-trifluoromethyl-phenyl)-carbamic acid 1-benzyl-1, 2, 3, 4-tetrahydro-quinolin-6-yl ester 2l. (4-bromo-phenyl)-carbamic acid 1-benzyl-1, 2, 3, 4-tetrahydro-quinolin-6-yl ester 2m. hexyl-carbamic acid 1-methyl-1, 2, 3, 4-tetrahydro-quinolin-6-yl ester 2n. heptyl-carbamic acid 1-methyl-1, 2, 3, .sup.4-tetrahydro-quinolin-6-yl ester 2o. (2-chloro-phenyl)-carbamic acid . -methyl-1, 2, 3, 4-tetrahydro-quinolin-6-yl ester 2p. (3-bromo-phenyl)-carbamic acid 1-methyl-1, 2, 3,.sup.4-tetrahydro-quinolin-6-yl ester 2q. (4-chloro-3-trifluoromethyl-phenyl)-carbamic acid 1-methyl-1, 2, 3, 4-tetrahydro-quinolin-6-yl ester, and 2r. (4-bromo-phenyl)-carbamic acid 1-methyl-1, 2, 3, 4-tetrahydro-quinolin-6-yl ester 2. A process for the synthesis of the substituted carbamic acid quinoline ester of claim 1; the process comprising reacting a substituted phenol with an isocyanate in the presence of a base and at least one organic solvent.

3. A process as claimed in claim 2 wherein the base used is selected from the group consisting of an organic and an inorganic base.

4. A process as claimed in claim 2 wherein the organic solvent is selected from the group consisting of ether, tetrahydrofuran (THF), dimethylformamide (DMF), dioxane, dichloromethane and chloroform.

5. A process as claimed in claim 2 wherein the base is selected from the group consisting of sodium hydride, sodium hydroxide, triethylamine and pyridine.

6. A process as claimed in claim 2 wherein the reaction is carried out at a temperature in the range of −10° C. to 80° C. and for a period between half an hour to 100 hours.

7. A process as claimed in claim 2 wherein the reaction is carried out in the presence of a catalyst selected from the group consisting of sodium iodide and potassium iodide.

8. A process as claimed in claim 2 wherein the molar ratio of substituted phenol to isocyanate is in the range of 1:1 to 1:1.2.

9. A process as claimed in claim 2 wherein the organic solvent is present in an amount in the range of 1.0 ml to 10 ml per mmol of the reactants.

10. A process for the synthesis of a quinoline derivative, the process comprising reacting a substituted phenol with an isocyanate in the presence of a base and at least one organic solvent to obtain the corresponding carbamic acid ester (carbamate), wherein the quinoline derivative is selected from the group consisting of:

2g. heptyl-carbamic acid 1-benzyl-1, 2, 3, 4-tetrahydro-quinolin-6-yl ester 2h. hexyl-carbamic acid 1-benzyl-1, 2, 3, 4-tetrahydro-quinolin-6-yl ester 2i. (2-chloro-phenyl)-carbamic acid 1-benzyl-1, 2, 3, 4-tetrahydro-quinolin-6-yl ester 2j. (3-bromo-phenyl)-carbamic acid 1-benzyl-1, 2, 3, 4-tetrahydro-quinolin-6-yl ester 2k. (4-chloro-3-trifluoromethyl-phenyl)-carbamic acid 1-benzyl-1, 2, 3, 4-tetrahydro-quinolin-6-yl ester 2l. (4-bromo-phenyl)-carbamic acid 1-benzyl-1, 2, 3, 4-tetrahydro-quinolin-6-yl ester 2m. hexyl-carbamic acid 1-methyl-1, 2, 3, 4-tetrahydro-quinolin-6-yl ester 2n. heptyl-carbamic acid 1-methyl-1, 2, 3, 4-tetrahydro-quinolin-6-yl ester 2o. (2-chloro-phenyl)-carbamic acid 1-methyl-1, 2, 3, 4-tetrahydro-quinolin-6-yl ester 2p. (3-bromo-phenyl)-carbamic acid 1-methyl-1, 2, 3, 4-tetrahydro-quinolin-6-yl ester 2q. (4-chloro-3-trifluoromethyl-phenyl)-carbamic acid 1-methyl-1, 2, 3, 4-tetrahydro-quinolin-6-yl ester 2r. (4-bromo-phenyl)-carbamic acid 1-methyl-1, 2, 3, 4-tetrahydro-quinolin-6-yl ester are obtained from 2a-f 2a. hexyl-carbamic acid 1, 2, 3, 4-tetrahydro-quinolin-6-yl ester 2b. heptyl-carbamic acid 1, 2, 3, 4-tetrahydro-quinolin-6-yl ester 2c. (3-bromo-phenyl)-carbamic acid 1,2,3,4-tetrahydro-quinolin-6-yl ester 2d. (2-chloro-phenyl)-carbamic acid 1, 2, 3, 4-tetrahydro-quinolin-6-yl ester 2e. (4-chloro-3-trifluoromethyl-phenyl)-carbamic acid 1, 2, 3, 4-tetrahydro-quinolin-6-yl ester 2f (4-bromo-phenyl)-carbamic acid 1, 2, 3, 4-tetrahydro-quinolin-6-yl ester by first reacting compounds 2a-l with an alkyl or aralkyl halide of formula RX wherein R is at least methyl or benzyl group and X is selected from the group consisting of chloro, bromo and iodio using a solvent selected from group consisting of dimethylformamide, tetrahydrofuran and dioxane, in the presence of an organic or inorganic base selected from the group consisting of sodium hydride, sodium hydroxide, triethylamine and pyridine and at a temperature ranging between −10° C. to 37° C. for a period of 1 hour to 12 hours in the presence or absence of a catalyst sodium iodide or potassium iodide.

11. A process as claimed in claim 2 wherein compounds of formulae 2a-f are synthesized from 2m-r using Pd—C 5-10% catalyst in a solvent selected from group consisting of ethanol and methanol in an amount of 15-25 ml per mmol of compound, by applying hydrogen pressure in the range of 50-60 psi for a period between 4-12 hours at room temperature.

12. A process as claimed in claim 2 wherein the phenol is reacted with an isocyanate to obtain corresponding carbamate which is then reduced with Ni—Al alloy/KOH/ethanol to give corresponding 1, 2, 3, 4-tetrahydro derivatives of formula 2a-l.

13. A process as claimed in claim 2 wherein the phenol is reacted with an isocyanate to obtain corresponding N-benzyl derivatives 2m-r which are then debenzylated using 5% or 10% Pd—C/$H_2$ in ethanol or methanol as solvent to obtain the corresponding debenzylated carbamates of formulae 2a-f, which are then N-methylated using MeI to give compounds of formulae 2m-r.

14. A process as claimed in claim 2 wherein compounds of formulae 2a-I are methylated in the presence of a solvent selected from the group consisting of tetrahydrofuran, dioxane and dimethylformamide and at a temperature ranging from 10° C. to 37° C., for between 3 hours to 48 hours.

15. A method for cognitive enhancement and treatment of a subject suffering from Alzheimer's or senile dementia, comprising administering a pharmaceutically effective amount of a compound of claim 1.

16. A method as claimed in claim 15 wherein the subject is a mammal.

17. A method as claimed in claim 16 wherein the mammal is a human being.

* * * * *